(12) United States Patent
Hsu (10) Patent No.: US 11,083,236 B2
(45) Date of Patent: Aug. 10, 2021

(54) MEASUREMENT GARMENT AND MEASURING SYSTEM

(71) Applicant: Sabrina Fashion Industrial Corp., New Taipei (TW)

(72) Inventor: Yu-Ming Hsu, New Taipei (TW)

(73) Assignee: Sabrina Fashion Industrial Corp., New Taipei (TW)

(*) Notice: Subject to any disclaimer, the term of this patent is extended or adjusted under 35 U.S.C. 154(b) by 127 days.

(21) Appl. No.: 16/568,263

(22) Filed: Sep. 12, 2019

(65) Prior Publication Data

US 2021/0076764 A1 Mar. 18, 2021

(51) Int. Cl.
*A41H 1/10* (2006.01)
*A61B 5/107* (2006.01)

(52) U.S. Cl.
CPC .............. *A41H 1/10* (2013.01); *A61B 5/107* (2013.01)

(58) Field of Classification Search
CPC ..... A61B 5/107; A61B 5/1072; A61B 5/1073; A41H 1/10
USPC ................... 33/16, 1 B, 1 K, 1 BB, 11, 512
See application file for complete search history.

(56) References Cited

U.S. PATENT DOCUMENTS

| | | | | |
|---|---|---|---|---|
| 3,327,394 A * | 6/1967 | Tenteris | .......... | A41H 1/02 33/2 R |
| 3,832,780 A * | 9/1974 | Lewis | .......... | A41H 1/02 33/2 R |
| 3,979,831 A * | 9/1976 | Lutz | .......... | A41H 3/00 33/17 R |
| 4,635,367 A * | 1/1987 | Vigede | .......... | A41H 1/02 33/15 |
| 4,823,476 A * | 4/1989 | Curtin | .......... | A41H 1/02 33/1 K |
| 4,875,296 A * | 10/1989 | Holzmeister | .......... | G01B 3/004 33/770 |
| 6,415,199 B1 * | 7/2002 | Liebermann | .......... | A41H 1/02 33/512 |
| 6,751,877 B2 * | 6/2004 | Grove | .......... | A41H 1/02 33/11 |
| 8,307,560 B2 * | 11/2012 | Tulin | .......... | G06Q 30/0201 33/17 R |
| 2014/0360030 A1 * | 12/2014 | Grove | .......... | A41H 3/04 33/17 R |
| 2016/0165988 A1 * | 6/2016 | Glasgow | .......... | G01B 21/20 703/11 |
| 2018/0010902 A1 * | 1/2018 | Gong | .......... | A61B 5/1072 |
| 2020/0367590 A1 * | 11/2020 | Istook | .......... | A41H 1/02 |

FOREIGN PATENT DOCUMENTS

| | | | | |
|---|---|---|---|---|
| GB | 2581361 A * | 8/2020 | .......... | A41H 1/10 |
| WO | WO-2019162547 A1 * | 8/2019 | .......... | A41H 1/02 |

* cited by examiner

*Primary Examiner* — Christopher W Fulton
(74) *Attorney, Agent, or Firm* — JCIPRNET (57) ABSTRACT

The disclosure provides a measurement garment and a measuring system. The measurement garment includes a first recognition pattern. The first recognition pattern is disposed at a stretchable part of the measurement garment, wherein the first recognition pattern comprises a first reference point and a second reference point, the stretchable part corresponds to a body part of a wearer wearing the measurement garment, and a specific distance between the first reference and a second reference point varies in response to the body part, and a variation of the specific distance is used for measuring a dimension of the body part.

17 Claims, 7 Drawing Sheets

MEASUREMENT GARMENT AND MEASURING SYSTEM

BACKGROUND OF THE INVENTION

1. Field of the Invention

The present disclosure generally relates to a measurement garment and a measuring system, in particular, to a measurement garment and a measuring system that measure the dimension of body part based on the variation of specific patterns on the measurement garment.

2. Description of Related Art

Smart clothes, also frequently referred to as high tech clothing, smart garments, or smart wear, are clothing items that have been modified by technology to be capable of performing some specific functions, such as heart rate monitoring, body temperature monitoring, etc. However, it seems that there are no smart clothing can be used for measuring human body.

SUMMARY OF THE INVENTION

Accordingly, the present invention is directed to a measurement garment and a measuring system, which may be used to solve the above issues.

The disclosure provides a measurement garment. The measurement garment includes a first recognition pattern. The first recognition pattern is disposed at a stretchable part of the measurement garment, wherein the first recognition pattern comprises a first reference point and a second reference point, the stretchable part corresponds to a body part of a wearer wearing the measurement garment, and a specific distance between the first reference and a second reference point varies in response to the body part, and a variation of the specific distance is used for measuring a dimension of the body part.

The disclosure provides a measuring system including a measurement garment and a measuring device. The measurement garment includes a first recognition pattern. The first recognition pattern is disposed at a stretchable part of the measurement garment, wherein the first recognition pattern comprises a first reference point and a second reference point, the stretchable part corresponds to a body part of a wearer wearing the measurement garment, and a specific distance between the first reference and a second reference point varies in response to the body part. The measuring device is configured to obtain a dimension of the body part based on a variation of the specific distance after capturing the first recognition pattern.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

Figure 1:
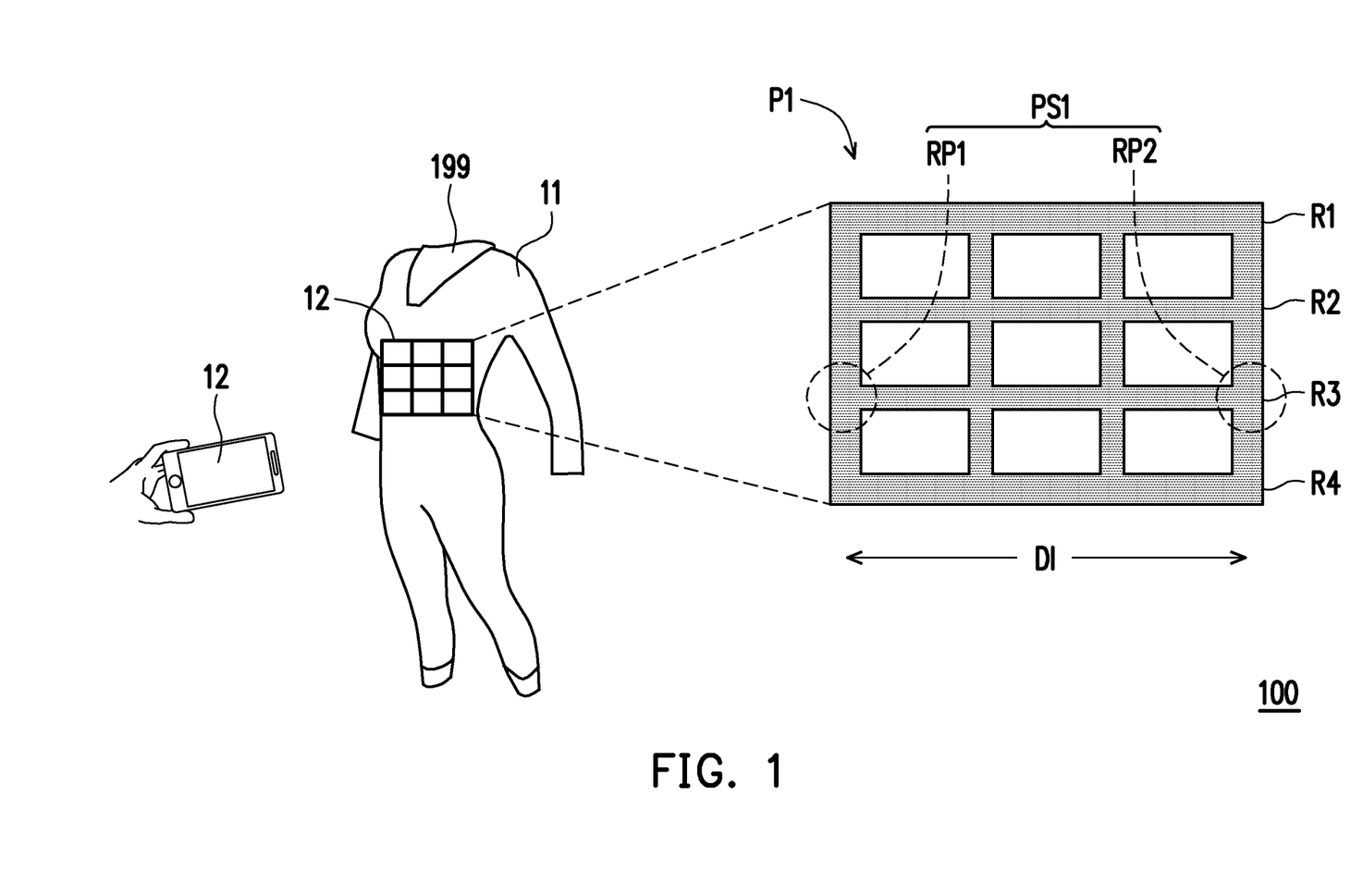
FIG. 1, which shows a schematic diagram illustrating a measuring system according to an exemplary embodiment of the disclosure.

See FIG. 1, in the present embodiment, a measuring system 100 includes a measurement garment 11 and a measuring device 12. In various embodiments the measurement garment 11 may be regarded as a smart clothing that is made by (partially) stretchable fabrics and could be worn by a human 199. In various embodiments, the measurement garment 11 could be implemented in many forms, such as a long-sleeve T-shirt, a short-sleeve T-shirt, a sleeveless T-shirt, a trouser, one-piece garment, long T-shirt that covers the hips, etc.

As shown in FIG. 1, the measurement garment 11 may be disposed with a recognition pattern P1, which may be disposed (e.g., printed) at a stretchable part of the measurement garment 11 and have a plurality of reference points (which may at least include a first reference point RP1 and a second reference point RP2). In the embodiment of FIG. 1, the recognition patter P1 may be implemented as a grid, and the reference points may correspond to the intersections therein. In other embodiments, the recognition patter P1 may be implemented as other appearances such as a dot matrix or a pattern, as long as there are at least two reference points existing therein.

In various embodiments, the measuring device 12 may be a smart phone, a tablet, a notebook, or other devices disposed with image capturing unit capable of taking pictures of the recognition pattern P1. The image capturing unit could also be capable of obtaining depth information, such as stereo vision, time-of-flight (ToF), and structured light (SL). Roughly speaking, in the embodiments of the disclosure, when the measurement garment 11 is worn by a human, the measuring device 12 may be used to obtain the dimension of the corresponding human part based on the variation of the distances between the reference points.

Based on the location of the recognition pattern P1 on the measurement garment 11, the to-be-measured dimension will be changed correspondingly. For example, if the measurement garment 11 is implemented as a form of T-shirt, the recognition pattern P1 may disposed at the chest area and/or the upper back area of the T-shirt for measuring the girth around the chest, which may be regarded as the chest circumference. For another example, if the measurement garment 11 is implemented as a form of T-shirt, the recognition patter P1 may be disposed at the belly area and/or the lower back area of the T-shirt for measuring the girth around the waist, which may be regarded as the waist circumference.

If the measurement garment 11 is implemented as a form of pants, the recognition patter P1 may disposed at the hip area of the pants for measuring the girth around the hips, which may be regarded as the hip circumference. If the measurement garment 11 is implemented as a form of pants, the recognition patter P1 may disposed at the thigh area and/or the hamstring area of the pants for measuring the girth around the thigh, which may be regarded as the thigh circumference. If the measurement garment 11 is implemented as a form of pants, the recognition patter P1 may disposed at the calve area of the pants for measuring the girth around the calve, which may be regarded as the calve circumference.

In some embodiments, one measurement garment proposed in the disclosure may be disposed with multiple recognition patterns disposed at the positions corresponding to the to-be-measured dimensions. For example, a measurement garment implemented as a form of T-shirt may have two recognition patterns respectively disposed at the chest area and the belly area for measuring the chest circumference and the waist circumference. For another example, a measurement garment implemented as a form of pants may have three recognition patterns respectively disposed at the hip area, the thigh area, and the calve area for measuring the hip circumference, the thigh circumference, and the calve circumference.

In one embodiment, before the measurement garment 11 is worn by the human 19, the first reference point RP1 may be spaced from the second reference point RP2 by a specific distance DI. In the present embodiment, the specific distance DI may be the distance between the centers of the first reference point RP1 and the second reference point RP2. After the measurement garment 11 is worn by the human 199, the measurement garment 11 may be uniformly stretched to fit the body shape of the human 199. Therefore, the specific distance DI would be enlarged in response to the corresponding body part of the human 199. In one embodiment, the measurement garment 11 needs to be stretched by at least 10% for a more accuracy measurement result.

In FIG. 1, since the recognition patter P1 may be regarded as being disposed at the belly area of the measurement garment 11, the corresponding body part of the recognition pattern P1 may be the waist of the human 199. In this case, after the measurement garment 11 is worn by the human 199, the specific distance DI would be enlarged in response to the waist of the human 199, and hence a variation of the specific distance DI may used for measuring a dimension of the body part, such as the girth around the waist, which may be referred to as the waist circumference of the human 199.

In the following, how and where the recognition patter P1 and the reference points therein would be firstly introduced, and the way of obtaining the dimension of the body part based on the variation of the specific distance DI would be discussed later in the disclosure.

As shown in FIG. 1, the first reference point RP1 and the second reference point RP2 may be horizontally arranged, and the girth around the corresponding body part may be accordingly measured based on the variation of the specific distance DI.

In other embodiments, the first reference point RP1 and the second reference point RP2 may be defined to form a reference point set PS1. As can be observed in FIG. 1, the recognition pattern P1 includes rows R1-R4, and each row R1-R4 of the recognition pattern P1 may be regarded as including multiple horizontally arranged reference point sets, and each row R1-R4 may be referred to as a measuring row for facilitating the following discussions.

In one embodiment, the variation of the specific distance DI related to the reference point set PS1 may be regarded as being used to obtain a value of the girth around the body part. Accordingly, the specific distances related to other reference point sets on the same measuring row may also be used to obtain other values of the girth around the body part as well. That is, the reference point sets on the same measuring row may be used to obtain multiple values of the girth around the same body part. In this case, these values may be averaged to a candidate girth around the body part, which may be regarded as a more statistically objective girth.

Moreover, as shown in FIG. 1, the recognition patter P1 may include multiple measuring rows R1-R4 which are vertically arranged. In this case, the user (e.g., the human 199) may choose the measuring row R1 based on the considered body part. Specifically, for measuring the accurate girth around the body part, there are some principles to follow.

For example, if the user wants to measure the waist circumference thereof by using a tape measure, the user has to put the tape measure around where the belly button locates. Accordingly, if the recognition pattern P1 including the measuring rows is used to measure the waist circumference, the user may choose one of the measuring rows that corresponds to where the belly button locates, such that the candidate girth of the chosen measuring row may be used as the accurate waist circumference, but the disclosure is not limited thereto.

For another example, if the user wants to measure the chest circumference thereof by using a tape measure, the user has to put the tape measure around where the nipples locate. Accordingly, if the recognition pattern P1 including the measuring rows is used to measure the chest circumference (which means that the recognition pattern P1 needs to be disposed at the chest area or the upper back area of the measurement garment 11), the user may choose one of the measuring rows that corresponds to where the nipples locate, such that the candidate girth of the chosen measuring row may be used as the accurate chest circumference, but the disclosure is not limited thereto.

In addition, since the first reference points RP1 and the second reference point RP2 that are horizontally arranged may be used to obtain the girth around the corresponding body part, in other embodiments, the first reference points RP1 and the second reference point RP2 may be modified to be vertically arranged for measuring a length of the corresponding body part.

In one embodiment, an undulation of the body part on which the first recognition pattern is disposed is smooth. That is, the position of the recognition pattern P1 on the measurement garment 11 may correspond to a smooth body part of the human 199, such as the waist area, the upper back area, the hip area, etc. Specifically, if the position of the recognition pattern P1 on the measurement garment 11 correspond to unsmooth body part of the human 199, the recognition pattern P1 may not be able to properly stretched in response to the corresponding body part. For example, if the recognition pattern P1 is used to measure the chest circumference of a woman, the recognition pattern P1 may be disposed at the upper back area of the measurement garment 11, instead of the chest area of the measurement garment 11, because the undulation of the breast of the woman may affect the stretching condition of the recognition pattern P1. In addition, for solving this issue, the disclosure also proposes an embodiment by disposing a non-stretchable part on the measurement garment, and where the non-stretchable part locates corresponds to the unsmooth body part.

In one embodiment, the position of where the recognition pattern P1 locates may have no suture, such that the stretching condition of the recognition pattern P1 may be maintained.

In one embodiment, since the recognition pattern P1 may be disposed on the measurement garment 11 with openings, such as sleeveless T-shirt, where the first reference point RP1 and the second reference point RP2 locate may not correspond to the openings to prevent the openings from affecting the stretching condition of the recognition pattern P1.

Figure 2A:
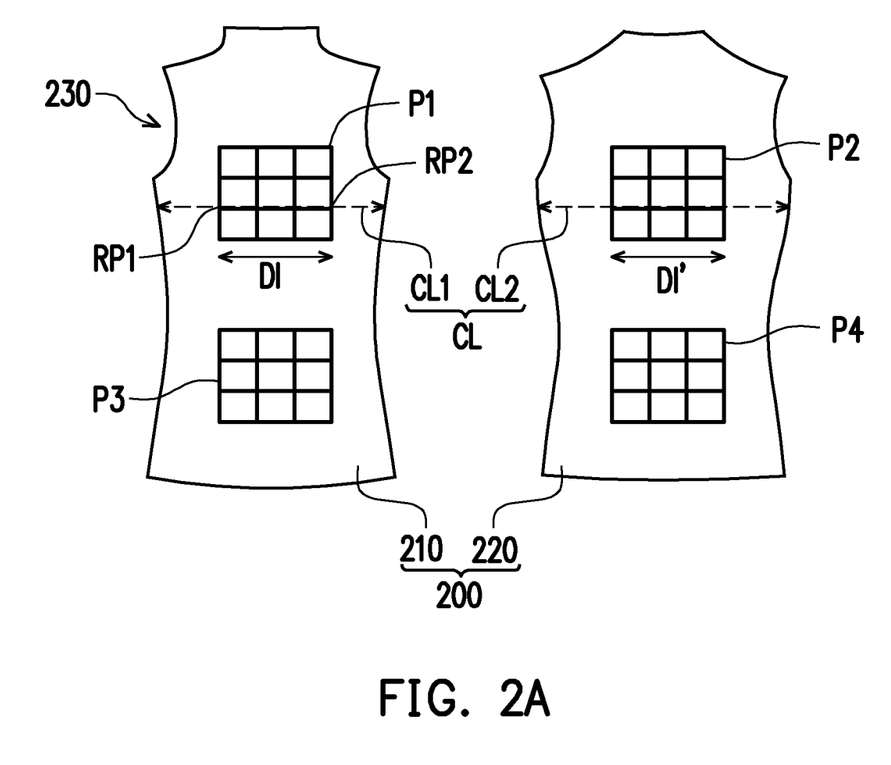
FIG. 2A is a schematic view showing pieces of the measurement garment according to an exemplary embodiment of the disclosure.
Figure 2B:
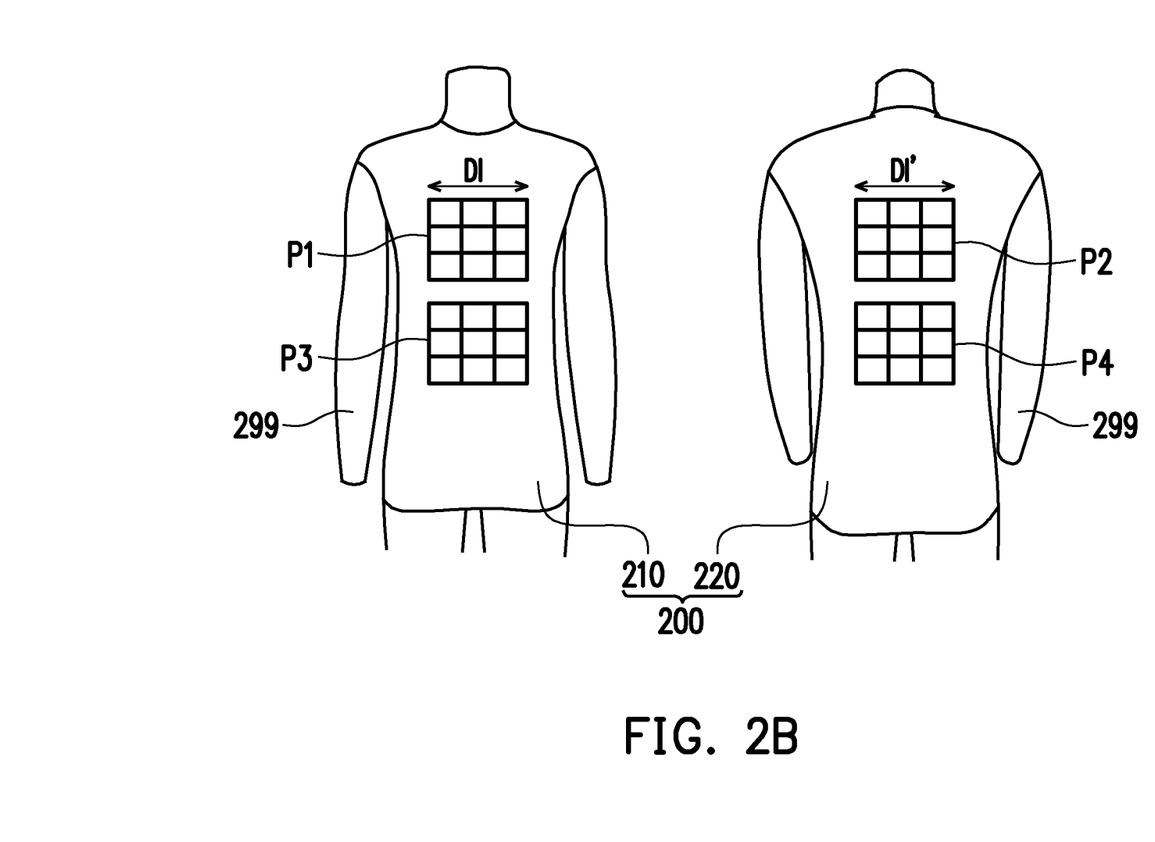
FIG. 2B is a schematic view showing the scenario of the measurement garment being worn according to FIG. 2A.

As shown in FIGS. 2A and 2B, a measurement garment 200 may include a front piece 210 and a back piece 220 that may be spliced together as the measurement garment 200. In the present embodiment, the measurement garment 200 may include recognition patterns P1, P2, P3, P4 that are disposed at the chest area, the upper back area, the belly area, and the lower back area, respectively. As taught in the above, the recognition patterns P1 and P2 may be (collectively) used to obtain the chest circumference, and the recognition patters P3 and P4 may be (collectively) used to obtain the waist circumference.

Specifically, in FIG. 2A, when the measurement garment 200 is not worn, the specific distance DI between the first reference point RP1 and the second reference point RP2 may be a first value. In addition, as shown in FIG. 2A, the first reference point RP1 and the second reference point RP2 may be regarded as being disposed on a circumferential line CL of the measurement garment 200. The circumferential line CL may include a first part CL1 disposed at the front piece 210 and a second part CL2 disposed at the back piece 220, and the first part CL1 and the second part CL2 may have a first width (which may be represented by $B_{CF}$) and a second width (which may be represented by $B_{CB}$), respectively.

In FIG. 2B, after the measurement garment 200 is worn by the human 299, the measurement garment 200 would be uniformly stretched in response to the body shape of the human 299, such that the recognition patterns P1-P4 would be stretched correspondingly. Therefore, the specific distance DI related to the recognition pattern P1 would be enlarged from the first value to be a second value. Similarly, a specific distance DI' related to the recognition pattern P2 would be enlarged from the first value to be a third value.

Accordingly, in a first embodiment, the dimension of the body part (i.e., the chest circumference of the human 299) may be obtained based on the first value, the second value, a length of the circumferential line CL, and a corrected parameter. For example, the chest circumference may be calculated as $$\left[\left(\frac{A'}{A}\right) \times B\right] \times K,$$

wherein A is the first value, A' is the second value, B is the length of the circumferential line CL (which is a sum of $B_{CF}$ and $B_{CB}$), and K is the corrected parameter. In various embodiments, the corrected parameter may be determined based on the characteristics of the fabric and textile of the measurement garment 200.

In the first embodiment, all of the above calculation may be performed by the measuring device 12 of FIG. 1 after taking pictures of the recognition patterns P1-P4 after the measurement garment 200 has been worn by the human 299. For performing the calculations, the default values of the measurement garment 200, such as the first value, the first width, the second width, the corrected parameter, etc. may be pre-stored in the measuring device 12.

To be more specific, for obtaining the chest circumference, the measuring device 12 may be used to take a picture of the recognition patter P1 in FIG. 2B. With the picture, the measuring device 12 may perform related image processing to obtain the second value based on the stretched (or distorted) recognition pattern P1. For example, the measuring device 12 may retrieve depth information of the picture and convert the first reference point RP1 and the second reference point RP2 as coordinates on a coordinate system. Accordingly, the measuring device 12 may obtain the second value based on the depth information and the coordinates (e.g., differences between the coordinates), such that the chest circumference could be calculated.

In addition, since there are multiple measuring rows in the recognition pattern P1, the measuring device 12 may obtain the candidate girth of each measuring rows, such that the user may be able to choose the one that could represent the actual chest circumference.

Alternatively, in a second embodiment, the dimension of the body part (i.e., the chest circumference of the human 299) may be alternatively obtained based on the first value, the second value, the third value, the first width, the second width, and a corrected parameter. For example, the chest circumference may be calculated as $$\left[\left(\frac{A1'}{A}\right) \times B_{CF}\right] \times K + \left[\left(\frac{A2'}{A}\right) \times B_{CB}\right] \times K,$$

wherein A is the first value, A1' is the second value, A2' is the third value, $B_{CF}$ is the first width, $B_{CB}$ is the second width, and K is the corrected parameter. In various embodiments, the corrected parameter may be determined based on the characteristics of the fabric and textile of the measurement garment 200.

In other embodiments, as mentioned before, the measurement garment may be disposed with a non-stretchable part, and hence the mechanism of obtaining the dimension of the corresponding body part may be correspondingly modified.

Figure 3A:
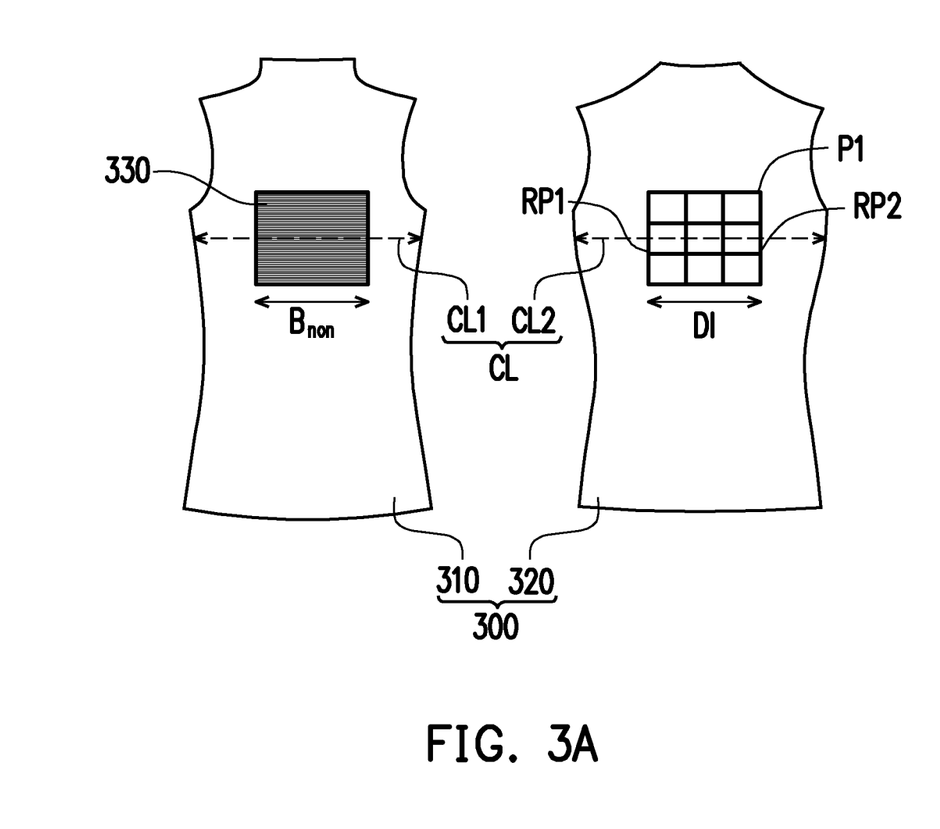
FIG. 3A is a schematic view showing pieces of the measurement garment according to an exemplary embodiment of the disclosure.
Figure 3B:
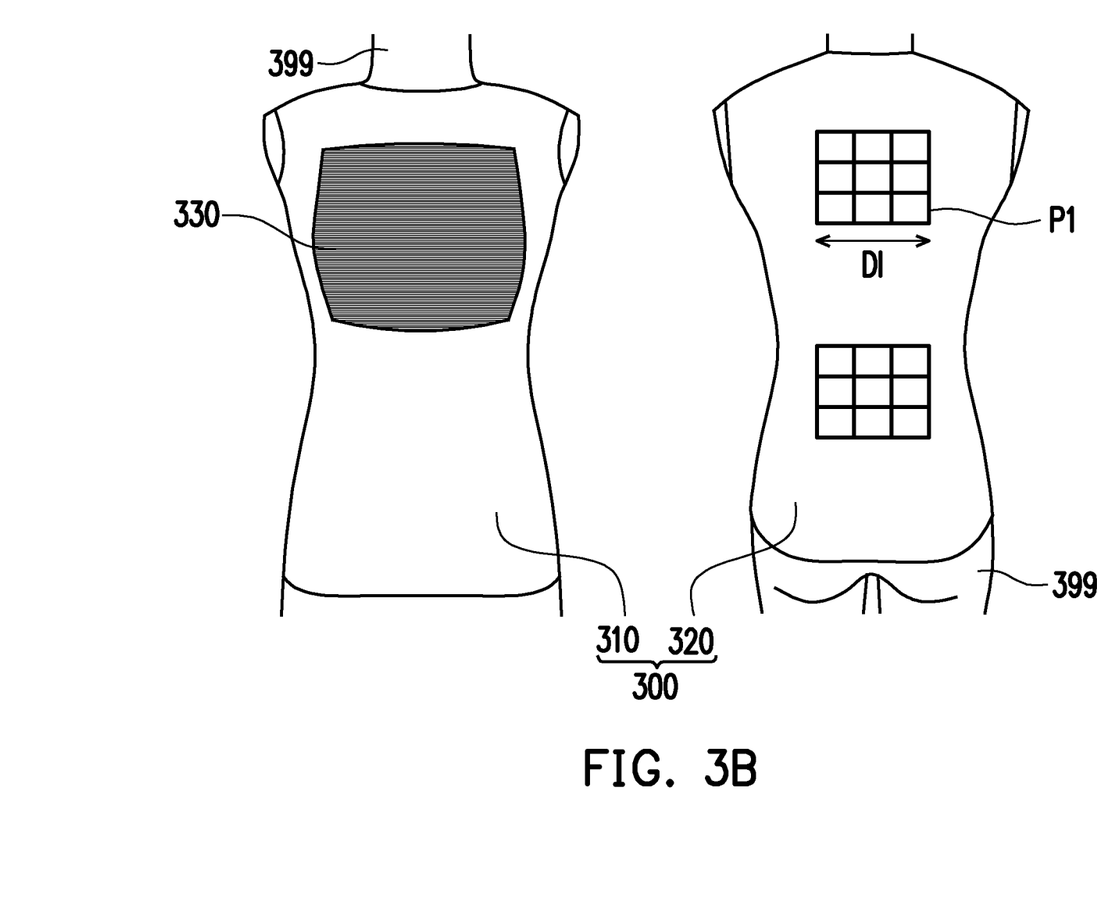
FIG. 3B is a schematic view showing the scenario of the measurement garment being worn according to FIG. 3A.

As shown in FIGS. 3A and 3B, the measurement garment 300 may include recognition patterns P1 disposed at the upper back area and a non-stretchable part 330 disposed at the chest area which is opposite to where the recognition pattern P1 locates on the measurement garment 300. In the present embodiment, the non-stretchable part 330 may have a specific width, which may be represented by $B_{non}$. As taught in the above, the recognition pattern P1 may be used to obtain the chest circumference.

Specifically, in FIG. 3A, when the measurement garment 300 is not worn, the specific distance DI between the first reference point RP1 and the second reference point RP2 may be a first value. In addition, as shown in FIG. 3A, the first reference point RP1 and the second reference point RP2 may be regarded as being disposed on a circumferential line CL of the measurement garment 300. The circumferential line CL may include a first part CL1 disposed at the front piece 310 and a second part CL2 disposed at the back piece 320, and the first part CL1 and the second part CL2 may have a first width (which may be represented by $B_{CF}$) and a second width (which may be represented by $B_{CB}$), respectively.

In FIG. 3B, after the measurement garment 300 is worn by the human 399, the measurement garment 300 would be uniformly stretched in response to the body shape of the human 399, such that the recognition pattern P1 would be stretched correspondingly. Therefore, the specific distance DI related to the recognition pattern P1 would be enlarged from the first value to be a second value.

Accordingly, the dimension of the body part (i.e., the chest circumference of the human 399) may be obtained based on the first value, the second value, a length of the circumferential line CL excluding the specific width (i.e., $B_{non}$), and a corrected parameter. For example, the chest circumference may be calculated as $$\left[\left(\frac{A'}{A}\right) \times B\right] \times K + B_{non},$$

wherein A is the first value, A' is the second value, B is the length of the circumferential line CL excluding the specific width (i.e., $B_{CF+}B_{CB}-B_{non}$), and K is the corrected parameter.

In some embodiments, since the measurement garment of the disclosure is made of stretchable fabric, the stretchable fabric may be loosen due to being repeatedly worn by various users, which may distort the proportion of the recognition pattern. As a result, the accuracy of the measured dimension of the corresponding body part would be sabotaged. Accordingly, the disclosure proposes another solution for fixing this issue.

Figure 4:
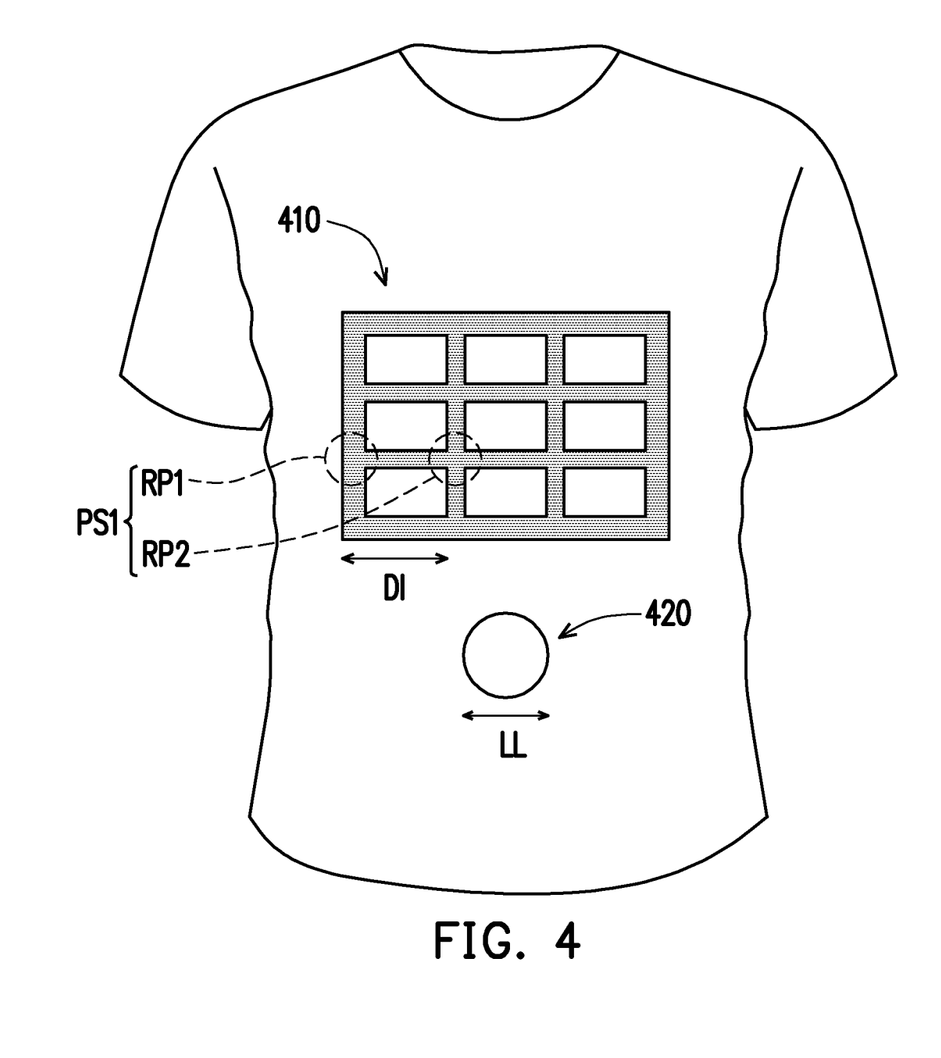
FIG. 4 shows a recognition pattern and a non-deformable object according to an exemplary embodiment of the disclosure.

See FIG. 4, a measurement garment may be disposed with a recognition pattern P1 and a non-deformable object 420. The recognition pattern 410 may have a first reference point RP1 and a reference RP2 which are spaced from each other by a specific distance DI. The non-deformable object 420 may be a button, a rivet, or other objects that will not be deformed and has a constant dimension.

In the present embodiment, a dimension LL (e.g., a diameter) of the non-deformable object 420 may be identical to the specific distance DI, and a ratio between the dimension LL and the specific distance DI, which may be distorted over time, may be used to correct the measured dimension of the corresponding body part.

For example, assuming that the specific distance DI has been distorted from a first distance to a second distance, a ratio between the second distance and the dimension LL may be obtained. Meanwhile, the dimension of the body part corresponding to the recognition pattern 410 with the distorted specific distance DI may be still measured based on the teachings above. After the dimension of the body part has been obtained, the dimension of the body part may be further corrected based on the ratio. For example, if the second distance is larger than the dimension LL by 10%, the dimension of the body part may be corrected by being decreased by 10% to generate an accurate data.

Figure 5:
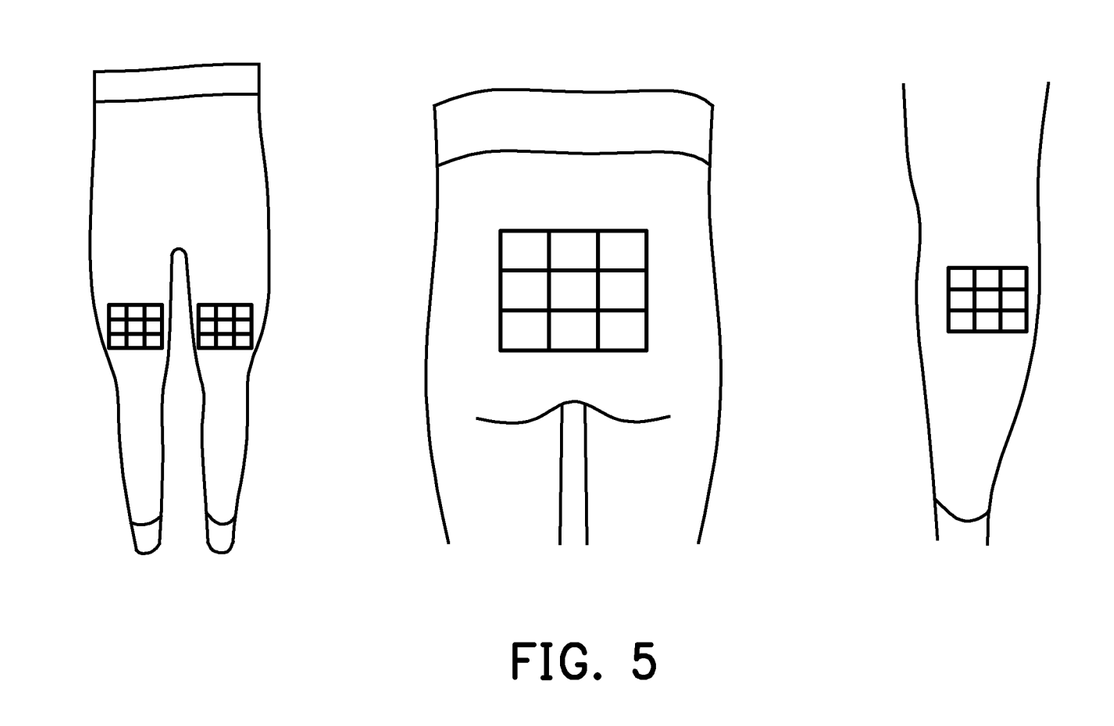
FIG. 5 shows various positions of recognition patterns according to exemplary embodiments of the disclosure.

See FIG. 5, which shows various positions of recognition patterns according to exemplary embodiments of the disclosure. As shown in FIG. 5, based on the to-be-measured dimension of the body part, the recognition patterns on the measurement garment (which may be implemented in a form of a trouser) may be disposed at the hip area, the thigh areas, and the calve area.

To sum up, since the measurement garment of the disclosure is disposed with one or more recognition patterns, the dimension of the body part(s) corresponding thereto may be obtained based on the distortion of the recognition patterns. More specifically, the dimension of the body part(s) corresponding thereto may be obtained based on the variation of the specific distance between the first reference point and the second point. Accordingly, the disclosure provides a novel, smart, convenient way to measure the dimensions of body parts.

Moreover, with the dimensions of the body parts, the type of the body shape of the wearer of the measurement garment may be retrieved. In this way, services and functions such as clothes suggestions, body shape monitoring, and body size data base collections may be achieved.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A measurement garment, comprising:
a first recognition pattern, disposed at a stretchable part of the measurement garment, wherein the first recognition pattern comprises a first reference point and a second reference point, the stretchable part corresponds to a body part of a wearer wearing the measurement garment, and a specific distance between the first reference and a second reference point varies in response to the body part, and a variation of the specific distance is used for measuring a dimension of the body part; and
a non-deformable object having a constant dimension, and the dimension of the body part is corrected based on a ratio between the constant dimension and the specific distance.

2. The measurement garment according to claim 1, wherein the first reference point and the second reference point are horizontally arranged, and the variation of the specific distance is used for measuring a girth around the body part.

3. The measurement garment according to claim 2, wherein the first reference point and the second reference point form a reference point set, and the first recognition pattern further comprises a plurality of the reference point sets that are horizontally arranged as a measuring row.

4. The measurement garment according to claim 3, wherein the specific distance of each of the reference point sets are used to obtain a plurality of values of the girth around the body part, and the values are averaged to obtain a candidate girth around the body part.

5. The measurement garment according to claim 3, wherein the first recognition pattern includes a plurality of the measuring rows which are arranged vertically, in response to one of the measuring row is chosen by the wearer.

6. The measurement garment according to claim 1, wherein the first reference point and the second reference point are vertically arranged, and the variation of the specific distance is used for measuring a length of the body part.

7. The measurement garment according to claim 1, wherein an undulation of the body part on which the first recognition pattern is disposed is smooth.

8. The measurement garment according to claim 1, wherein the first reference point and the second reference point are arranged on a circumferential line of the measurement garment, and the measurement garment has no opening on the circumferential line.

9. The measurement garment according to claim 1, wherein the measurement garment includes a front piece and a back piece, the front piece has a non-stretchable part, the first recognition pattern is disposed at the back piece and opposite to the non-stretchable part.

10. The measurement garment according to claim 9, wherein the non-stretchable part has a specific width, the first reference point and the second reference point are arranged on a circumferential line of the measurement garment, and in response to the specific distance is changed from a first value to be a second value, the girth around the body part is obtained based on the first value, the second value, a length of the circumferential line excluding the specific width, and a corrected parameter.

11. The measurement garment according to claim 1, wherein the first reference point and the second reference point are arranged on a circumferential line of the measurement garment, and in response to the specific distance is changed from a first value to be a second value, the dimension of the body part is obtained based on the first value, the second value, a length of the circumferential line, and a corrected parameter.

12. The measurement garment according to claim 1, wherein the measurement garment comprises a front piece and a back piece, and the measurement garment further comprises a second recognition pattern identical to the first recognition pattern, the first recognition pattern is disposed at one of the front piece and the back piece, the second recognition pattern is disposed at another of the front piece and the back piece, and the first recognition pattern and the second recognition pattern are opposite to each other;

wherein the first reference point and the second reference point on each of the first recognition pattern and the second recognition pattern are arranged on a circumferential line of the measurement garment, the circumferential line comprises a first width of the front piece and a second width of the back piece, and in response to the specific distance related to the first recognition pattern is changed from a first value to be a second value and the specific distance related to the second recognition pattern is changed from the first value to a third value, the dimension of the body part is obtained based on the first value, the second value, the third value, the first width, the second width, and a corrected parameter.

13. A measurement system, comprising:
a measurement garment, comprising:
a first recognition pattern, disposed at a stretchable part of the measurement garment, wherein the first recognition pattern comprises a first reference point and a second reference point, the stretchable part corresponds to a body part of a wearer wearing the measurement garment, and a specific distance between the first reference and a second reference point varies in response to the body part;

a non-deformable object having a constant length, and the measuring device corrects the dimension of the body part based on a ratio between the constant length and the specific distance; and a measuring device, configured to obtain a dimension of the body part based on a variation of the specific distance after capturing the first recognition pattern.

14. The measurement system according to claim 13, wherein the measurement garment includes a front piece and a back piece, the front piece has a non-stretchable part, the first recognition pattern is disposed at the back piece and opposite to the non-stretchable part.

15. The measurement system according to claim 14, wherein the non-stretchable part has a specific width, the first reference point and the second reference point are arranged on a circumferential line of the measurement garment, and in response to the specific distance is changed from a first value to be a second value, the measuring device obtains the girth around the body part based on the first value, the second value, a length of the circumferential line excluding the specific width, and a corrected parameter.

16. The measurement system according to claim 13, wherein the first reference point and the second reference point are arranged on a circumferential line of the measurement garment, and in response to the specific distance is changed from a first value to be a second value, the measuring device the dimension of the body part based on the first value, the second value, a length of the circumferential line, and a corrected parameter.

17. The measurement system according to claim 13, wherein the measurement garment comprises a front piece and a back piece, and the measurement system further comprises a second recognition pattern identical to the first recognition pattern, the first recognition patter is disposed at one of the front piece and the back piece, the second recognition pattern is disposed at another of the front piece and the back piece, and the first recognition pattern and the second recognition pattern are opposite to each other;

wherein the first reference point and the second reference point on each of the first recognition pattern and the second recognition pattern are arranged on a circumferential line of the measurement garment, the circumferential line comprises a first width of the front piece and a second width of the back piece, and in response to the specific distance related to the first recognition pattern is changed from a first value to be a second value and the specific distance related to the second recognition pattern is changed from the first value to a third value, the dimension of the body part is obtained based on the first value, the second value, the third value, the first width, the second width, and a corrected parameter.

* * * * *